United States Patent
Anhalt et al.

[11] Patent Number: 5,976,190
[45] Date of Patent: Nov. 2, 1999

[54] ORTHOPAEDIC CONNECTION

[75] Inventors: Klaus-Peter Anhalt, Rhumspringe; Juergen Deinert, Duderstadt, both of Germany

[73] Assignee: Otto Bock Orthopaedische Industrie Besitz- Und Verwaltungs-Kommanditgesellschaft, Duderstadt, Germany

[21] Appl. No.: 08/965,355

[22] Filed: Nov. 6, 1997

[30] Foreign Application Priority Data

Nov. 6, 1996 [DE] Germany ............................ 196 45 679

[51] Int. Cl.⁶ .................................................. A61F 2/60
[52] U.S. Cl. .................................. 623/28; 623/27; 623/38
[58] Field of Search ................... 623/27, 28, 38

[56] References Cited

U.S. PATENT DOCUMENTS

| | | | |
|---|---|---|---|
| 2,923,947 | 2/1960 | Weighill | 623/28 |
| 4,118,806 | 10/1978 | Porier et al. | 623/1 |
| 5,037,144 | 8/1991 | Peting | 285/321 |
| 5,181,850 | 1/1993 | Neumeyer | 433/205 |
| 5,571,211 | 11/1996 | Hiemisch et al. | 623/38 |
| 5,800,563 | 9/1998 | Arbogast et al. | 623/38 |

FOREIGN PATENT DOCUMENTS

| | | |
|---|---|---|
| 0 694 295 | 1/1996 | European Pat. Off. . |
| 38 10 857 | 6/1989 | Germany . |
| 41 39 700 | 4/1993 | Germany . |
| 89/05161 | 6/1989 | WIPO . |

OTHER PUBLICATIONS

Abstract of EP 0694295 A2 to Hiemisch et al. Jan. 1996.

*Primary Examiner*—Paul B. Prebilic
*Attorney, Agent, or Firm*—Foley & Lardner

[57] ABSTRACT

The invention relates to an orthopaedic clamped connection as a functional element for force transmission in a prosthesis, comprising a tube socket and a tube made of light metal. To increase the dynamic stressability, the contact area between tube socket and tube made of light metal is provided with an intermediate layer which is composed of a low molecular weight carrier material in which at least one lubricant and/or auxiliary is embedded.

22 Claims, 2 Drawing Sheets

ORTHOPAEDIC CONNECTION

Background of the Invention

The present invention relates to an orthopaedic clamped connection as a functional element for force transmission in a prosthesis, of the general type comprising a tube socket and a tube made of light metal.

Such a clamped connection is described in EP-A2 0 694 295. This document discloses an axially slit tube socket which can be circumferentially tensioned by means of a clamping screw. The socket is adjoined at one end by an annular coupling section which on its circumference has four threaded holes, each to accommodate a coupling and adjustment screw, and on the end face has an annular ball socket to rest against a ball joint of an adjustment body which, in the coupling position, has a projection configured as a multiface pyramid projecting into the clamping region of the clamping screw. The free end section of the tube socket opposite the coupling section is provided on its inner annular surface with a plastic clamping sleeve which can be configured as a separate ring or as an inner coating. The axial length of the plastic clamping sleeve corresponds approximately to one fifth of the axial length of the tube socket. As a result of this design, clamping no longer occurs directly at the end of the tube but at a distance therefrom, so that the tube section lying between the plastic clamping sleeve and the coupling section can be subjected to elastic deformation. In the region of the highest relative movement between the tube socket and tube end, metallic contact between these two parts is prevented by the plastic clamping sleeve. Dynamic flexural tests have shown that this considerably increases the life of said components.

This previously known solution has been found to be useful in principle, but other disadvantages have to be accepted in order to attain the advantages mentioned. Thus, the sleeve as a separate plastic ring requires a lengthening of the adapter and thus higher manufacturing costs and a higher weight. The plastic sleeve itself can have stresses and can be out-of-round as a result of the manufacturing process, which can lead to problems in assembly. When the sleeve is configured as a plastic layer, the achievable tolerances are unsatisfactory; an excess therefore has to be applied and subsequently machined away. Moreover, a plastic sleeve can suppress frictional corrosion to only a limited extent.

SUMMARY OF THE INVENTION

It is therefore an object of the present invention to provide an improved orthopaedic clamped connection.

A further object of the invention is to improve the clamped connection described in the introduction in respect of a higher dynamic stressability and at the same time ensure good releaseability between adapter and tube made of light metal even after long-term use.

In accomplishing these objects, there has been provided according to the present invention an orthopaedic clamped connection as a functional element for force transmission in a prosthesis, comprising a tube socket and a tube made of light metal, forming a contact area therebetween, wherein the contact area includes an intermediate layer comprising a low molecular weight carrier material in which at least one lubricant and/or auxiliary is embedded.

Further objects, features and advantages of the present invention will become apparent from the detailed description of preferred embodiments that follows, when considered together with the attached figures of drawings.

DETAILED DESCRIPTION OF PREFERRED EMBODIMENTS

Figure 1:
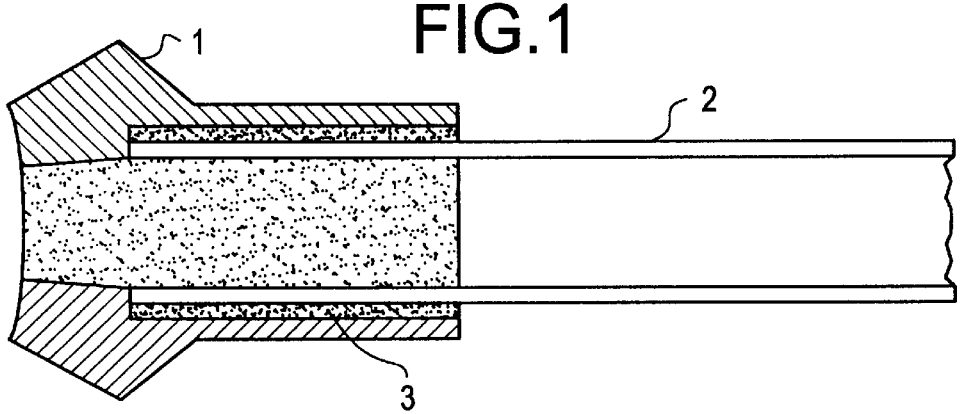
FIG. 1 shows a schematic longitudinal section of an orthopaedic clamped connection.

According to the invention, the contact area between tube socket and tube made of light metal is provided with an intermediate layer which is composed of a low molecular weight carrier material in which lubricants and/or auxiliaries are embedded.

For the purposes of the present invention, the term "low molecular weight" means a molecular weight which is less than in the case of polymeric materials and should thus be less than 5000 g/mol.

The function of the carrier material is to provide bonding to the substrate, to provide mechanical strength and to provide wear resistance. Suitable materials for use as the carrier include inorganic materials, such as a metal, a metal salt, a metal oxide or a ceramic material. Preferred materials include metal sulfates, metal aluminates, metal silicates, a ferrite, nickel, steel and/or phosphorus.

Lubricants prevent metallic frictional contact, protect the tube surface from mechanical damage, make possible stick-slip-free micromovements, lead to a reduction in the coefficient of friction and also reduce frictional corrosion. It has surprisingly been found here that the dynamic structural strength of the clamping connection can be significantly increased by the addition of lubricants. The surface roughness of a metal surface usually suffices to accommodate sufficient lubricants. Suitable lubricants include a dicarboxylic ester, a fatty acid, a fatty acid ester, a fatty acid amide, a metal soap, a silicone oil, molybdenum sulfide, a polyolefin wax, a paraffin, a fluoropolymer, or a combination thereof.

Auxiliaries provide compatibility and bonding (adhesion) between lubricant, carrier material and/or adapter material or tube material, or further functions, e.g., protection against oxidation, wetting of surfaces, etc.

In those embodiments in which a lubricant is used alone, without addition of an adhesion-promoting binder or wetting agent, a lubricant which adheres by itself to metal surfaces, for example, $MoS_2$, should be used. The layer thicknesses that can be achieved in this way are naturally only very small (about 1 µm); despite this, however, an improvement in the dynamic structural strength has been able to be determined. This is explained by the fact that further lubricant can be supplied to the interface from the pores of the metal surfaces.

In addition, it has been found that the amount of lubricant adsorbed can be increased by addition of a wetting agent and that an increase in the lubrication time can thus be achieved.

An improved dynamic structural strength can also be achieved by completely or partially replacing the lubricant by one or more antioxidants. This effect can only be explained by the antioxidants not only reducing the frictional corrosion but also being able to suppress sliding back in the case of micromovements between the tube made of light metal and the tube socket. Suitable antioxidants include an alkylphenol, a hydroxyphenyl propionate, an hydroxybenzyl, an alkylidenebisphenol, a thiobisphenol, a secondary aromatic amine, an aminophenol, a sterically hindered amine, a phosphite or a phosphonite.

The layer thickness can be increased by addition of a binder, which means better separation of the metal surfaces. In addition, higher layer thicknesses are necessary if the layer is to have an electrically insulating action to avoid contact corrosion. According to one embodiment, the intermediate layer is configured as an insulation layer having a volume resistance of $>10^{10}$ $\Omega mm^2$. As a result of the use of binder systems, the lubricant can also be held better on the interface, which simplifies reusability. In addition, when using binder systems it is also possible to employ low-viscosity lubricants.

Binder systems allow the build-up of layer thicknesses of up to 1 mm, which allows manufacturing tolerances to be compensated for and uniform force transmission to be achieved. However, in the case of higher layer thicknesses, not only the tribological properties but also the mechanical properties of the lubricant-binder system are of importance, with especially the viscosity and the cold flow behavior influencing the dynamic structural strength of the clamped connection.

The binder system used can comprise very different materials; only the compatibility with the lubricants used and the adhesion to the metal substrate when configured as a coating have to be ensured. Both inorganic and organic binders have been found to be useful. Inorganic binders and thermosetting resins have been found to be particularly advantageous for producing layers up to 50 μm. Suitable thermosetting resins include a phenolformaldehyde resin (PF), a urea-formaldehyde resin (UF), a melamine-formaldehyde (MF), an unsaturated polyester resin (UP), an epoxy resin (EP) or a crosslinked polyurethane resin. On the other hand, thermoplastic binders and binders based on tar are, owing to the viscosity and the flow behavior, suitable for layer thicknesses up to 1 mm. Suitable thermoplastic resins include an ethylenevinyl acetate copolymer (EVA), a polyamide 11, a polyamide 12, a polyvinylidene fluoride polymer (PVDF), a tetrafluoroethylene-hexafluoropropylene copolymer, or polychlorotrifluoroethylene (PCTFE).

The type and concentration of lubricant and binder enable a defined coefficient of friction to be set. This must normally not drop below $\mu=0.3$ under use conditions, since otherwise sufficient force can no longer be transmitted. In the case of fluorine-containing binder systems (e.g. FEP, PCTFE), the binder/lubricant ratio can become very great; e.g., the ratio for the combination FEP/silicone oil can be up to 50:1.

Apart from the use of lubricants and/or antioxidants, it has also been found to be useful to use friction materials in the layer between tube made of light metal and tube socket. These materials prevent micromovements between the tube and socket when the prosthesis is dynamically stressed. They therefore have a mechanism of action which is opposite to that of the lubricants and can be compared in their functionality and their make-up with materials for brake elements. Suitable materials include mineral fibers, glass fibers, carbon fibers, metal fibers, barium sulfate or ground stone.

However, increasing the static friction by establishing geometric interlocking has been found to be particularly advantageous. For this purpose, the intermediate layer has to incorporate materials which are incompressible, have a higher hardness than the tube made of light metal to be clamped and at the same time form a strong bond with the core material of the tube socket. In the clamping process, the roughness peaks of the intermediate layer can then be pressed into the surface of the tube made of light metal, thus establishing geometric interlocking.

However, friction layers which act by means of geometric interlocking have been found to be abrasive if the increased static friction is overcome by application of an excessively high torque, and micromovements in the clamped connection occur.

It has therefore been found, even in the case of the friction layers, to be advantageous to incorporate lubricants into the pores. If movements occur between the tube made of light metal and the intermediate layer, these lubricants are pushed out of the pores and thus reduce abrasive damage if the prosthesis is overloaded. In practice, an intermediate layer built up in this way has an increased coefficient of static friction and at the same time a reduced coefficient of sliding friction.

Even in the case of friction materials, it can be advantageous to suppress corrosion by means of complete or partial replacement of the lubricant by antioxidants.

The application of the lubricant layer according to the invention can be carried out using different methods, depending on the system. Low-viscosity systems can be applied in a targeted way using a brush or sponge. Dipping, rubbing or spray processes are also conceivable. The surface usually does not have to be pretreated; however, degreasing should be carried out in the embodiment as a coating. The lubricant layer can be applied by means of automated manufacturing processes, but also manually.

The following embodiments have been found to be particularly advantageous:

EXAMPLE 1

| | |
|---|---|
| Material of tube socket: | Steel |
| Material of tube element: | Aluminum |
| Layer thickness: | about 1 μm |
| Carrier material: | 50% of steel |
| Lubricant: | 49% of $MoS_2$ |
| Wetting agent (auxiliary): | 1% of alkylbenzenesulfonate |

EXAMPLE 2

| | |
|---|---|
| Material of tube socket: | Steel |
| Material of tube element: | Aluminum |
| Layer thickness: | about 4 μm |
| Carrier material: | 25% of barium sulfate |
| Lubricant: | 70% of $MoS_2$ |
| Antioxidant (auxiliary): | 5% of N,N'-dinaphthyl-p-phenylenamine (aromatic amine) |

EXAMPLE 3

| | |
|---|---|
| Material of tube socket: | Titanium |
| Material of tube element: | Aluminum |
| Layer thickness: | about 15 μm |
| Carrier material: | 25% of steel |
| First auxiliary: | 25% of unsaturated polyester resins |
| Lubricant: | 45% of PTFE/$MoS_2$ mixture |

-continued

| | |
|---|---|
| Antioxidant (2nd auxil.): | 5% of 2,6-di-tert-butyl-4-nonylphenol |

EXAMPLE 4

| | |
|---|---|
| Material of tube socket: | Aluminum |
| Material of tube element: | Aluminum |
| Layer thickness: | about 100 $\mu$m |
| Carrier material: | 30% of aluminum oxide |
| First auxiliary: | 40% of PVDF |
| Lubricant: | 10% of PTFE |
| | 10% of Li soap |
| Antioxidant (2nd auxil.): | 10% of Tris(2,4-di-t-butyl-phenyl)phosphite |

EXAMPLE 5

| | |
|---|---|
| Material of tube socket: | Steel |
| Material of tube element: | Aluminum |
| Layer thickness: | about 1 $\mu$m |
| Carrier material: | 50% of steel |
| Auxiliary: | 49% of PE wax |
| Lubricant | 1% of alkylbenzenesulfonate |

EXAMPLE 6

| | |
|---|---|
| Material of tube socket: | Steel |
| Material of tube element: | Aluminum |
| Layer thickness: | about 250 $\mu$m |
| Carrier material (friction layer): | 90% by weight of quartz/corundum |
| Lubricant: | 10% by weight of graphite |

EXAMPLE 7

| | |
|---|---|
| Material of tube socket: | Steel |
| Material of tube element: | Aluminum |
| Layer thickness: | about 1 mm |
| Sleeve: Carrier material: | 75% by weight of aluminum oxide |
| Lubricant: | 23% by weight of molybdenum sulfide |
| | 2% by weight of silicone oil |

Turning now to the drawings, FIG. 1 shows a schematic longitudinal section of an orthopaedic clamped connection as a functional element for force transmission in a prosthesis, comprising a tube socket 1 of titanium and an aluminum tube as tube made of light metal 2. Between these two components there is provided an intermediate layer 3 having a thickness of abut 50 $\mu$m.

Figure 2:
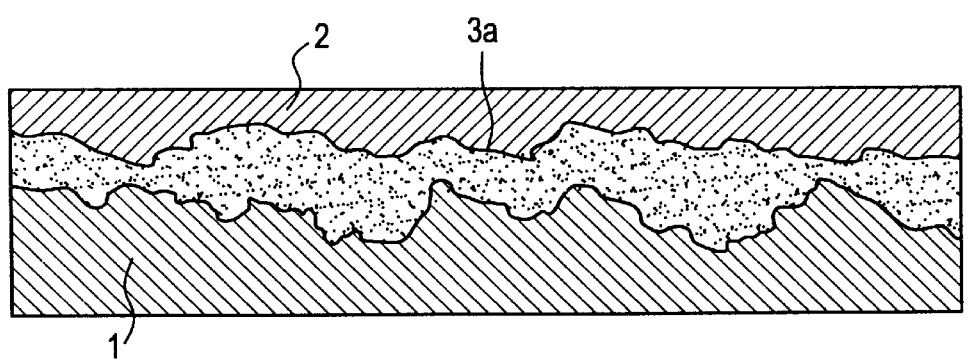
FIG. 2 shows a greatly enlarged view of the interface region depicted in FIG. 1.

FIG. 2 shows a greatly enlarged view of the interface region between tube socket 1 and tube made of light metal 2 depicted in FIG. 1, with the intermediate layer being composed of a carrier material with embedded MoS$_2$ as lubricant 3a.

Figure 3:
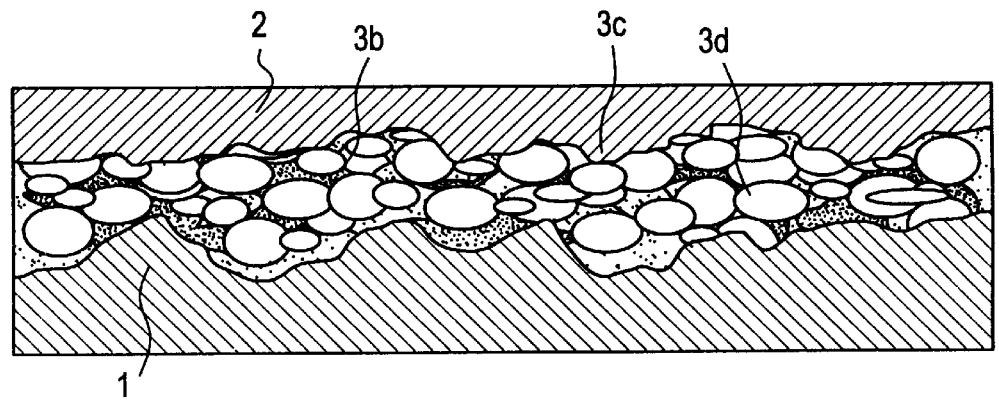
FIG. 3 shows, in a view similar to FIG. 2, the boundary layer between the tube socket and the tube.

FIG. 3 shows, in a depiction similar to FIG. 2, the boundary layer between the tube socket 1 and the tube made of light metal 2 with an intermediate lubricant layer of PTFE 3b and phosphite 3c, with polyester resin as an auxiliary and barium sulfate 3d as carrier material.

Figure 4:
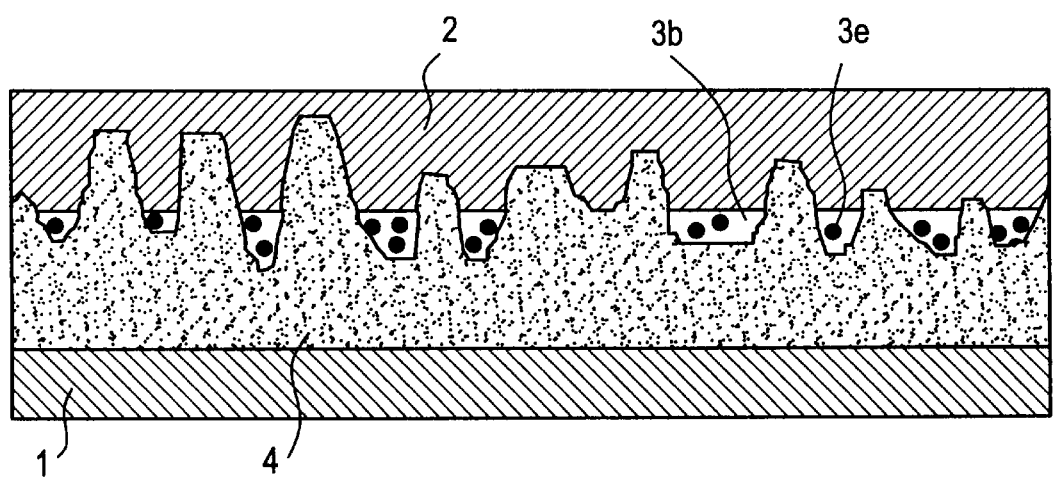
FIG. 4 shows, again, greatly enlarged, the boundary layer between the tube socket and the tube for another embodiment.

FIG. 4 shows, again, greatly enlarged, the boundary layer between the tube socket 1 and the tube made of light metal 2 with a siliceous carrier material 4 as well as PTFE 3b as lubricant and an alkylphenol 3e as antioxidant.

The invention has been described with reference to several preferred embodiments. It will be apparent that numerous modifications and substitutions of equivalent structures and materials can be made without departing from the general scope of the invention.

The entire disclosure of German Patent Application No. 196 45 679.7, filed Nov. 6, 1996, is hereby incorporated by reference.

What is claimed is:

1. An orthopaedic clamped connection as a functional element for force transmission in a prosthesis comprising a tube socket and a tube made of light metal, and a contact area therebetween, wherein the contact area includes an intermediate layer comprising a low molecular weight carrier material in which at least one of a lubricant or auxiliary is embedded, wherein the intermediate layer has a thickness of from 0.1 $\mu$m to 1 mm.

2. An orthopaedic clamped connection as claimed in claim 1, wherein the lubricant is at least one selected from the group consisting of a dicarboxylic ester, a fatty acid, a fatty acid ester, a fatty acid amide, a metal soap, a silicone oil and molybdenum sulfide.

3. An orthopaedic clamp connection as claimed in claim 1, wherein the lubricant is at least one selected from the group consisting of a polyolefin wax, a paraffin, and a fluoropolymer.

4. An orthopaedic clamped connection as claimed in claim 1, wherein the carrier material comprises an inorganic material.

5. An orthopaedic clamped connection as claimed in claim 4, wherein the carrier material comprises a metal, a metal salt, a metal oxide or a ceramic material.

6. An orthopaedic clamped connection as claimed in claim 1, wherein the carrier material comprises at least one of a sulfate, an aluminate, a silicate, a ferrite, nickel or phosphorus.

7. An orthopaedic clamped connection as claimed in claim 1, wherein the intermediate layer further comprises an antioxidant.

8. An orthopaedic clamped connection as claimed in claim 7, wherein the antioxidant comprises an alkylphenol, a hydroxyphenyl propionate, an hydroxybenzyl, an alkylidenebisphenol, a thiobisphenol, a secondary aromatic amine, an aminophenol, a sterically hindered amine, a phosphite or a phosphonite.

9. An orthopaedic clamped connection as claimed in claim 1, wherein the intermediate layer further comprises a wetting agent.

10. An orthopaedic clamped connection as claimed in claim 1, wherein the intermediate layer is anchored firmly as a coating on the tube socket or on the tube made of light metal.

11. An orthopaedic clamped connection as claimed in claim 1, wherein the intermediate layer is a separate sleeve.

12. An orthopaedic clamped connection as claimed in claim 1, wherein the auxiliary comprises an organic material.

13. An orthopaedic clamped connection as claimed in claim 12, wherein the organic auxiliary comprises tar.

14. An orthopaedic clamped connection as claimed in claim 12, wherein the organic material comprises a thermosetting resin.

15. An orthopaedic clamped connection as claimed in claim 14, wherein the thermosetting resin comprises a phenol-formaldehyde, a urea-formaldehyde, a melamine-formaldehyde, an unsaturated polyester resin, an epoxy resin or a crosslinked polyurethane.

16. An orthopaedic clamped connection as claimed in claim 12, wherein the organic material comprises at least one thermoplastic polymer.

17. An orthopaedic clamped connection as claimed in claim 16, wherein the thermoplastic polymer comprises an ethylene-vinyl acetate copolymer, a polyamide 11, a polyamide 12, a polyvinylidene fluoride, a tetrafluoroethylene-hexafluoropropylene copolymer, or polychlorotrifluoroethylene.

18. An orthopaedic clamped connection as claimed in claim 1, wherein the carrier material comprises a material which increases static friction.

19. An orthopaedic clamped connection as claimed in claim 18, wherein the friction material has a higher hardness than the tube made of light metal.

20. An orthopaedic clamped connection as claimed in claim 18, wherein the material which increases static friction comprises an inorganic material.

21. An orthopaedic clamped connection as claimed in claim 20, wherein the inorganic material comprises mineral fibers, glass fibers, carbon fibers, metal fibers, barium sulfate or ground stone.

22. An orthopaedic clamped connection as claimed in claim 1, wherein the intermediate layer is configured as an insulation layer having a volume resistance of $>10^{10}$ $\Omega mm^2$.

* * * * *